United States Patent [19]

Moore

[11] Plant 4,662

[45] Mar. 3, 1981

[54] MINIATURE ROSE PLANT

[76] Inventor: Ralph S. Moore, 2519 E. Noble Ave., Visalia, Calif. 93277

[21] Appl. No.: 115,742

[22] Filed: Jan. 28, 1980

[51] Int. Cl.[3] ..... A01H 5/00

[52] U.S. Cl. ..... Plt./7

[58] Field of Search ..... Plt./7

*Primary Examiner*—James R. Feyrer

[57] ABSTRACT

The subject of the present disclosure is a new and distinct variety of miniature rose plant characterized by soft yellow buds and flowers which are tinted with pink on edges and tips of petals.

1 Drawing Figure

1

The present invention relates to a new and distinct variety of hardy, dwarf, bush type rose plant of the miniature class; the variety being primarily characterized—as to novelty—by soft yellow buds and flowers which are tinted with pink along petal edges and tips, the general color effect resembling the Peace rose (Hybrid Tea—U.S. Plant Pat. No. 591, expired) only in miniature.

The variety is further characterized by:

An abundance of bloom, with flowers borne singly or several to the stem in loose clusters.

Little fragrance.

A plant which is vigorous, of rounded somewhat upright shape with semi-glossy to matt, small foliage with pointed leaflets; the buds and flowers being similar in coloring, form and size to Debbie (miniature—U.S. Plant Pat. No. 2,911).

The plant, which has a normal height of 14–16 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at Sequoia Nursery located at Visalia, Calif., under conditions of careful control and observation, as a cross between Little Darling (U.S. Plant Pat. No. 1,581, expired) as the seed parent and Yellow Magic, (miniature—not patented), as the pollen parent.

Subsequent to origination of the variety I successfully reproduced it, at Sequoia Nursery located as aforesaid, by budding as well as by cuttings; the reproductions having run true in all respects.

The color photograph illustrates the variety including the foliage, buds and flowers as it appears when grown outdoors (June 1979).

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy (somewhat upright); rounded; seedling; greenhouse; outdoors; cut flowers; garden decoration; potted plant.

Class: Miniature.

(*International identification, variety: Morliyel*).—Commercial synonym: Sierra Sunrise.

2

Flowers borne: Singly and in loose clusters of 3–5 or more on slender wirey stems.

Quantity of bloom: Abundant both outside and in greenhouse.

Bud:

*Peduncle.*—Medium to long; slender but sturdy; erect; medium green, sometimes tinted bronze (outdoors); hairs—(more like fuzz) fairly numerous.

*Before calyx breaks, size.*—Small. Form long; pointed with several foliaceous appendages and few tiny hairs on surface of bud; with foliaceous parts extending beyond the tip of the bud equal to one-half or less of its length. Color—medium green, occasionally tinted with bronze (outdoors).

*As calyx breaks, color.*—Pale green to soft yellow. Opening: opens well in all weather.

Bloom:

*Size when fully open.*—Small, averaging about 35–40 mm (1½").

*Petalage.*—Double—averaging about 35–40 petals, arranged regularly, plus sometimes several small petaloids.

*Form.*—Cupped to high centered at first, becoming more open in the center, with petals reflexing loosely outward, and later at maturity, open and rolled loosely outward and downward. Open flower may show stamens.

Petals: Fairly thick; satiny on inside and on outside surface.

*Shape.*—Outside petals, broad lanceolate (nearly oval) with very small (short) acute tip; intermediate—broad lanceolate with rounded or small acute tip; inside—lanceolate with rounded tip. Petals on mature flowers tend to fold back or quill, giving petals a very pointed appearance.

Color: Newly opened flower from a plant grown (A) in plastic greenhouse (October 1979), Visalia, Calif.

*Outside petals.*—Outside surface—near Sulphur Yellow ⅓ becoming slightly deeper yellow or greenish yellow at base.

*Intermediate petal.*—Outside surface—similar to outside petal. Inside surface—similar to outside petal.

*Inner petal.*—Outside surface—same as intermediate petal; inside surface—same as intermediate petal.

And (B) as grown outdoors in full sun (June 1979): Basic color same or similar to above but buds and flowers are brushed or tinted with pink along petal edges and petal tips (especially the outer row or rows) thus resembling the Peace rose (Hybrid Tea) or Debbie (miniature).

*General color effect newly opened flowers.*—In greenhouse; soft yellow to cream outdoors; soft yellow tinted pink.

*Three days open.*—Color similar to newly opened flowers but less brilliant (more cream).

*Behavior.*—Opens well in all weather. Spent petals drop off.

*Flower longevity* (May 1979).—Plant in pot 6–8 days or longer. Cut flowers at living room temperature 4–5 days or longer.

Reproductive organs:

*Stamens.*—Moderate number, arranged regularly about pistils.

*Filaments.*—Varying length, medium long, yellow.

*Anthers.*—Well formed; yellow.

*Pollen.*—Moderate amount.

*Pistils.*—Average number.

*Styles.*—Fairly even; medium to short length; bunched; color—pale greenish.

*Ovaries.*—All enclosed in calyx.

*Hips.*—Few or none.

*Sepals.*—Permanent; spear shaped; recurved.

*Seed.*—Few or none.

Foliage:

*Leaves.*—Compound of five (sometimes three or seven) leaflets; fairly small; leather; semi-glossy to matt.

*Leaflets.*—Shape: broad, lanceolate; apex acute; base rounded or rounded acute. Margin serrate. Color: medium green; new growth—normal (medium) green—sometimes reddish. Rachis: medium strength; upper side may have a few tiny short hairs, grooved; underside sparsely thorny with few or no tiny prickles. Stipules; medium long; narrow to medium width; medium length; narrow points which turn out usually at about 45 degrees.

Growth:

*Habit.*—Dwarf; bushy; upright rounded; much branched.

*Growth.*—Free vigorous; internodes short.

*Canes.*—Medium; slender; sturdy.

*Main stems.*—Color: medium green.

*Thorns.*—Average; slender; usually straight or inclined slightly downward; color, brown. Prickles—none. Hairs—none.

*Branches.*—Color: medium green. Thorns: moderate number; medium length; slender; nearly straight or inclined slightly downward. Long oval base. Prickles: none. Hairs: none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded, much branched habit, substantially as illustrated and described, characterized by buds and flowers of a soft yellow color being of a shade similar to Sulphur Yellow ⅓, the bud and flower resembling the variety Debbie (U.S. Plant Pat. No. 2,911) in form and size and, when grown outdoors, also resembling Debbie, in coloring; and further characterized by a plant of vigorous, compact growth habit, easy to propagate from cuttings or by budding, with an abundance of small to medium size semi-glossy to matt foliage and an abundance of flowers borne singly or in loose clusters of 3 to 5 or more.

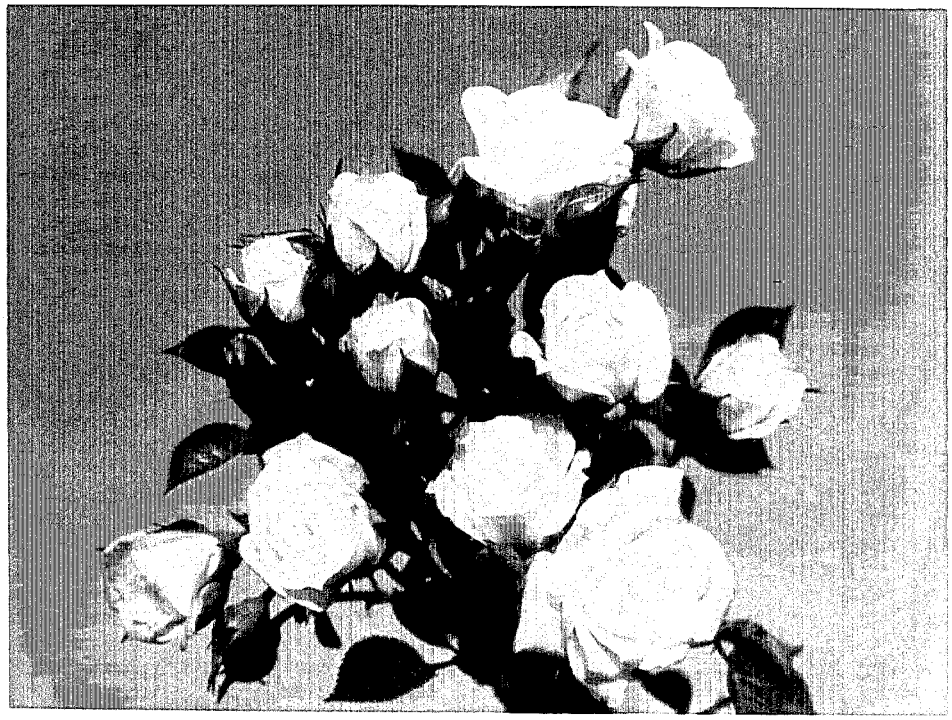

* * * * *